United States Patent
Howling et al.

(10) Patent No.: US 9,545,273 B2
(45) Date of Patent: Jan. 17, 2017

(54) POLYAXIAL LOCKING HOLE ARRANGEMENT

(75) Inventors: Ilan Howling, Kiel (DE); Claudia Graca, Kiel (DE); Annika Homeier, Kiel (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 177 days.

(21) Appl. No.: 14/343,876

(22) PCT Filed: Sep. 16, 2011

(86) PCT No.: PCT/EP2011/004658
§ 371 (c)(1),
(2), (4) Date: May 7, 2014

(87) PCT Pub. No.: WO2013/037387
PCT Pub. Date: Mar. 21, 2013

(65) Prior Publication Data
US 2014/0276828 A1    Sep. 18, 2014

(51) Int. Cl.
*A61B 17/56* (2006.01)
*A61B 17/72* (2006.01)
*A61B 17/17* (2006.01)

(52) U.S. Cl.
CPC ....... *A61B 17/7233* (2013.01); *A61B 17/1725* (2013.01); *A61B 17/72* (2013.01)

(58) Field of Classification Search
CPC .................................................. A61B 17/725
USPC .......................................... 606/287; 411/437
See application file for complete search history.

(56) References Cited

U.S. PATENT DOCUMENTS

| | | | |
|---|---|---|---|
| 4,622,959 A | * | 11/1986 | Marcus .............. A61B 17/1721 606/64 |
| 5,549,610 A | | 8/1996 | Russell et al. |
| 5,562,667 A | | 10/1996 | Shuler et al. |
| 5,709,686 A | | 1/1998 | Talos et al. |
| 6,210,414 B1 | | 4/2001 | Lin et al. |

(Continued)

FOREIGN PATENT DOCUMENTS

| | | |
|---|---|---|
| EP | 1557131 A1 | 7/2005 |
| EP | 1605845 A1 | 12/2005 |

(Continued)

OTHER PUBLICATIONS

Japanese Office Action for Application No. 2014-530101 dated Mar. 24, 2015.

(Continued)

*Primary Examiner* — Jan Christopher Merene
(74) *Attorney, Agent, or Firm* — Lerner, David, Littenberg, Krumholz & Mentlik, LLP

(57) ABSTRACT

An intramedullary nail according to the invention has a locking hole arrangement having one first opening on one side of the intramedullary nail and one second opening at an opposing side of the intramedullary nail. The locking hole arrangement has a first bore having a first bore axis and a second bore having a second bore axis. The first bore and the second bore each having a first orifice on one side of the intramedullary nail and each having a second orifice at an opposite side of the intramedullary nail. The first bore axis and the second bore axis are inclined with respect to each other and the first bore and the second bore intersect each other within the intramedullary nail.

18 Claims, 8 Drawing Sheets

(56) References Cited

U.S. PATENT DOCUMENTS

| | | | |
|---|---|---|---|
| 6,221,074 B1 | 4/2001 | Cole et al. | |
| 6,228,086 B1 | 5/2001 | Wahl et al. | |
| 6,322,562 B1* | 11/2001 | Wolter | A61B 17/72 606/287 |
| 7,041,104 B1 | 5/2006 | Cole et al. | |
| D536,453 S | 2/2007 | Young et al. | |
| 7,534,254 B1 | 5/2009 | Michelson | |
| 7,670,340 B2 | 3/2010 | Brivio et al. | |
| 7,695,472 B2 | 4/2010 | Young | |
| 7,740,648 B2 | 6/2010 | Young et al. | |
| 7,905,883 B2 | 3/2011 | Bruecker et al. | |
| 7,947,043 B2 | 5/2011 | Mutchler | |
| 8,100,953 B2 | 1/2012 | White et al. | |
| 8,771,271 B2* | 7/2014 | Overes | A61B 17/1725 606/62 |
| 2002/0058939 A1* | 5/2002 | Wagner | A61B 17/7059 606/86 B |
| 2004/0127901 A1* | 7/2004 | Huebner | A61B 17/8042 606/281 |
| 2005/0070904 A1 | 3/2005 | Gerlach et al. | |
| 2006/0095039 A1* | 5/2006 | Mutchler | A61B 17/72 606/64 |
| 2006/0111716 A1 | 5/2006 | Schlienger et al. | |
| 2006/0264946 A1* | 11/2006 | Young | A61B 17/1728 606/915 |
| 2007/0233100 A1 | 10/2007 | Metzinger | |
| 2010/0179550 A1* | 7/2010 | Schreiber | A61B 17/1725 606/62 |
| 2011/0087227 A1 | 4/2011 | Mazur et al. | |
| 2012/0123484 A1* | 5/2012 | Lietz | A61B 17/14 606/281 |

FOREIGN PATENT DOCUMENTS

| | | |
|---|---|---|
| EP | 1639953 A1 | 3/2006 |
| JP | 2000513593 A | 10/2000 |
| JP | 2003516170 A | 5/2003 |
| JP | 2005205214 A | 8/2005 |
| JP | 2006513781 A | 4/2006 |
| WO | 9613220 A1 | 5/1996 |
| WO | 2004082494 A1 | 9/2004 |

OTHER PUBLICATIONS

International Search Report and Written Opinion for Application No. PCT/EP2011/004658 dated Jun. 18, 2012.

* cited by examiner

POLYAXIAL LOCKING HOLE ARRANGEMENT

CROSS-REFERENCE TO RELATED APPLICATIONS

The present application is a national phase entry under 35 U.S.C. §371 of International Application No. PCT/EP2011/004658 filed Sep. 16, 2011, published on Mar. 21, 2013 as WO 2013/037387, all of which are hereby incorporated herein by reference.

BACKGROUND OF THE INVENTION

The invention generally relates to an intramedullary nail. Particularly, the invention relates to polyaxial locking hole arrangement provided at an end portion of an intramedullary nail for a femur, a humerus or a tibia.

In the field of intramedullary nailing screw placement is very important in order to fixate different fracture patterns and to avoid damaging soft tissue.

U.S. Pat. No. 7,695,472 B2 discloses a bone plate with a longitudinal axis having a bone-contacting bottom side and a top side. Sets of overlapping holes communicate through the plate from the top to the bottom side. The overlapping holes have multifaceted surfaces such as a threaded surface or a coaxial series of annular groves. The sets of overlapping holes are adapted to receive a bone screw with a head and a bone-engaging thread.

U.S. Patent Publication No. 2006/0111716 discloses an intramedullary nail with a distal end suitable for an insertion into the medullar space, wherein the segment of the intramedullary nail facing the distal end has a diameter D, a proximal end, a central longitudinal axis, and several cross holes with a hole axis, each of which defines a virtual drill cylinder with a cylinder axis corresponding to the hole axis of the defining cross hole, wherein the drill cylinders of at least two cross holes penetrate each other, the cylinder axis of the two mutually penetrating drill cylinders have no common intersection point P on the longitudinal axis. The cylinder axis of the two mutually penetrating drill cylinders lies in a plane orthogonal to the longitudinal axis.

In general, the proximal end of the bone is the end of the bone being oriented toward the heart of the human body. The distal end of the bone is the end of the bone being oriented away from the heart of the human body. An intramedullary nail may be a femur nail, a humerus nail or a tibia nail, wherein the intramedullary nail comprises a non-driving end portion and a driving end portion. The non-driving end portion is the end of the nail which firstly enters the intramedullary channel of a bone. Entering a bone from the proximal end of the bone is denoted as antegrade entering. Entering a bone from the distal end of the bone is denoted as retrograde entering. Consequently, a nail adapted to be implanted from the proximal end of the tibia may be denoted as antegrade tibia nail, a nail adapted to be implanted from the distal end of the femur may be denoted as retrograde femur nail, and a nail adapted to be implanted from the proximal end of the humerus may be denoted as antegrade humerus nail.

BRIEF SUMMARY OF THE INVENTION

It may be seen as one aspect of the invention to provide an intramedullary nail allowing for more flexible screw placement during surgery and thus enhance the patient outcome.

This is achieved by the subject-matter of each of the independent claims. Further embodiments are described in the respective dependent claims.

In general, an intramedullary nail according to a first aspect of the invention comprises a locking hole arrangement having a first opening on one side of the intramedullary nail and a second opening at an opposing side of the intramedullary nail, wherein the locking hole arrangement comprises a first bore having a first bore axis and a second bore having a second bore axis, wherein the first bore and the second bore each having a first orifice on one side of the intramedullary nail and each having a second orifice at an opposing side of the intramedullary nail, opposing on the circumference of the nail. The first bore axis and the second bore axis are inclined with respect to each other and the first bore and the second bore intersect each other.

The first orifice of the first bore and the first orifice of the second bore together form the first opening of the locking hole arrangement, and the second orifice of the first bore and the second orifice of the second bore together form a second opening of the locking hole arrangement. It will be understood, that the first orifice of the first bore overlap the first orifice of the second bore in such a configuration. The same counts for the respective second orifices.

Such polyaxial holes provide the following clinical benefits:
 Due to fracture lines, a variation of screw placement is possible.
 Due to sensible soft tissue structures like nerves, arteries and blood vessels, a variation of screw placement is possible, for example, in case of humeral bone in order to avoid damage to the ascending branch of the anterior circumflex artery.
 An analogy of screw placement in case of left and right bones and thus compatibility with one universal nail design for left and right bones is possible.

According to an embodiment of the invention, the locking hole arrangement is arranged in a driving end portion of the intramedullary nail. Advantageously, the locking hole arrangement may be arranged in a driving end portion of a humerus nail, a tibia nail or a femur nail.

According to an embodiment of the invention, the first bore axis and the second bore axis intersect each other, that is, the first bore axis and the second bore axis are also inclined with respect to each other.

It is noted, that the inclined axes may lie in a plane which is orientated substantially transverse or orthogonal to the longitudinal axis of intramedullary nail. That is, the width of the polyaxial hole arrangement may be larger in a circumferential direction of the nail than in a longitudinal direction of the nail. It will be understood, that the inclined axes may also lie in a plane which is orientated substantially parallel to the longitudinal axis of the nail, or inclined to said axis.

According to another embodiment of the invention, a minimum distance of the first bore axis and the second bore axis lies within the intramedullary nail. The minimum distance of the first bore axis and the second bore axis may lie on a longitudinal axis of the intramedullary nail.

The minimum distance of the first bore axis and the second bore axis is the shortest distance between the two lines defining the first and second bore axes. If the first bore axis and the second bore axis intersect or cross, the minimum distance is zero. If the first bore axis and the second bore axis are inclined with respect to each other, but do not intersect, i.e. the first and second bore axes are skew, the minimum distance is larger than zero. It should be understood that with respect to the axes also a distance of zero is considered as a minimum distance.

According to another embodiment of the invention, the first bore axis and the second bore axis are inclined with respect to each other, without intersecting each other. Furthermore, the first bore axis and the second bore axis may be orthogonal to a longitudinal centre axis of the intramedullary nail.

According to a second aspect of the invention, the locking hole arrangement comprises, in addition to the features of the intramedullary nail according to the first aspect of the invention, a third bore having a third bore axis, wherein the third bore has a first orifice on one side of the intramedullary nail and the second orifice at an opposing side of the intramedullary nail, opposing on the circumference of the nail. The first bore axis, the second bore axis and the third bore axis are inclined with respect to each other, and additionally intersect each other.

The first orifice of the first bore, the first orifice of the second bore, and the first orifice of the third bore together form the first opening of the locking hole arrangement, wherein the second orifice of the first bore, the second orifice of the second bore, and the second orifice of the third bore together form the second opening of the locking hole arrangement. It will be understood, that the first orifices of the first, second and third bore overlap each other. The same counts for the respective second orifices.

According to an embodiment of the invention, the first bore axis, the second bore axis, and the third bore axis intersect within the intramedullary nail. The first bore axis, the second bore axis, and the third bore axis may further intersect a longitudinal centre axis of the intramedullary nail. Furthermore, the first bore axis, the second bore axis, and the third bore axis may each be inclined with respect to each other and may each be orthogonal to a longitudinal centre axis of the intramedullary nail.

According to another embodiment of the invention, the third bore axis has an orientation corresponding to the medio-lateral direction.

According to yet another embodiment of the invention, the first bore axis is inclined by plus 15 degrees over the third bore axis, and the second bore axis is inclined by minus 15 degrees over the third bore axis.

At least one of the first opening and the second opening may comprise a chamfer with respect to the respective orifice of the first bore and/or with respect to the respective orifice of the second bore. Furthermore, at least one of the first bore, the second bore, and the third bore may comprise a thread.

According to another aspect of the invention, a combination of a targeting device and an intramedullary nail as described above is provided. The targeting device comprises a coupling portion being adapted to be coupled to the driving end of the intramedullary nail. The targeting device comprises a drilling gauge with a drilling axis corresponding to at least one of the first bore, the second bore, and the third bore of the intramedullary nail to be coupled to the targeting device.

According to yet another aspect of the invention, a method of fixating an intramedullary nail in a fractured bone is provided, wherein the method generally comprises the steps of introducing the intramedullary nail into the fractured bone, identified in a fracture line of the bone, selecting one bore of the bores of the polyaxial hole arrangement, and introducing a locking screw through the bone and the selected bore.

These aspects defined above and further aspects, features and advantages of the present invention can also be derived from the examples of the embodiments to be described hereinafter and are explained with reference to the examples of the embodiments to which the invention is not limited.

BRIEF DESCRIPTION OF THE DRAWINGS

The invention will now be detailed by way of an exemplary embodiment with reference to the attached drawings.

It is noted that the illustration of the drawings is only schematically and not to scale. In different figures, similar elements are provided with the same reference signs.

DETAILED DESCRIPTION

Figure 1:
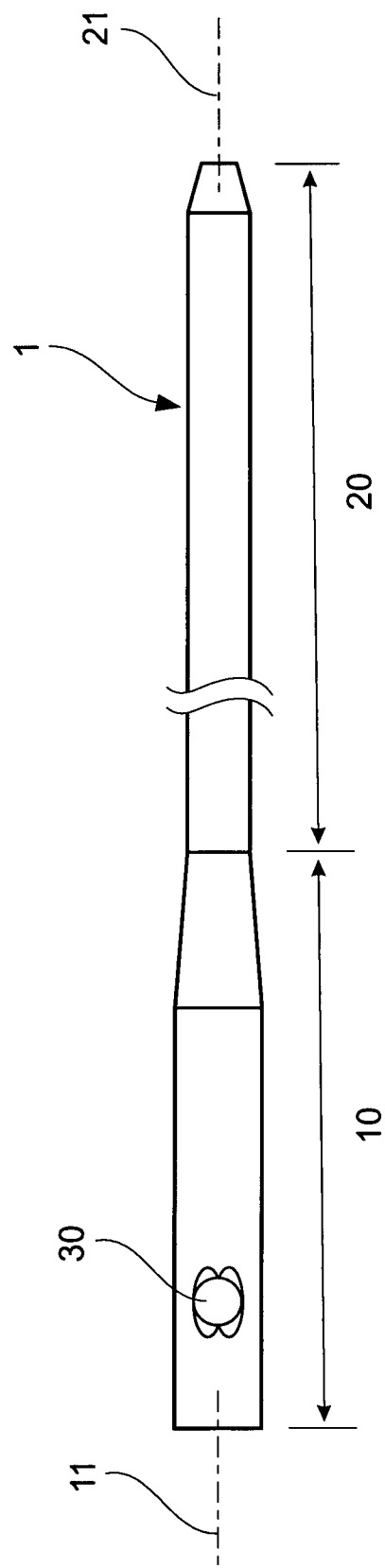
FIG. 1 is a side view of an intramedullary nail with a polyaxial hole arrangement at its driving end portion.

FIG. 1 shows an intramedullary nail 1 with a non-driving end portion 20 and a driving end portion 10, wherein a polyaxial hole arrangement 30 is provided in the driving end portion 10. The driving end portion 10 of the intramedullary nail 1 comprises a longitudinal axis 11, whereas the non-driving end portion 20 comprises a longitudinal axis 21. It is noted that the longitudinal axis of the driving end portion 10 may differ from the longitudinal axis 21 of the non-driving end portion 20, for example, in case that the intramedullary nail 1 is curved or bent.

Figure 2A:
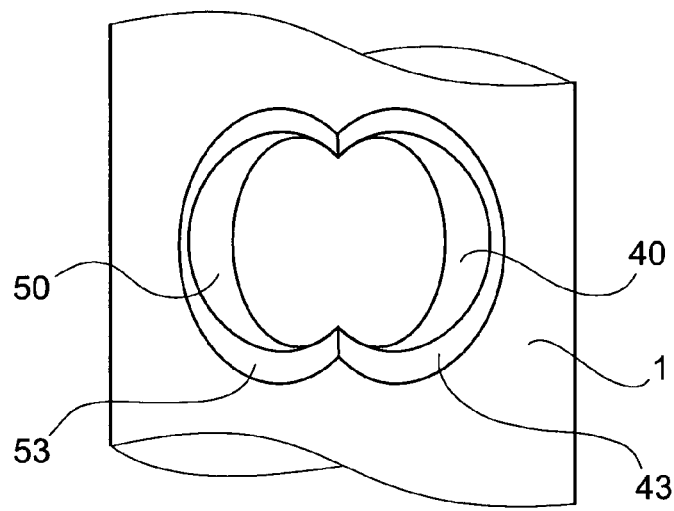
FIG. 2a is a detail view of a polyaxial hole arrangement with two bores.

FIGS. 2 to 5 illustrate a polyaxial hole arrangement according to the invention with two bores, being inclined with respect to each other, wherein the two bore axes intersect within the intramedullary nail In FIG. 2a, a polyaxial hole with a first bore 40 and a second bore 50 is illustrated. The intramedullary nail 1 is cut above and under the polyaxial hole arrangement. The first bore 40 is inclined with respect to the second bore 50 so that the polyaxial hole arrangement has a width in a horizontal direction which is larger than a heights in a vertical direction. To facilitate an introduction of a locking screw both the first bore 40 and the second bore 50 are provided with chamfers 43, 53, respectively. FIG. 2b differs from FIG. 2a in that the first bore 40 and second bore 50 are provided with threads 44 and 54, respectively.

Figure 3:
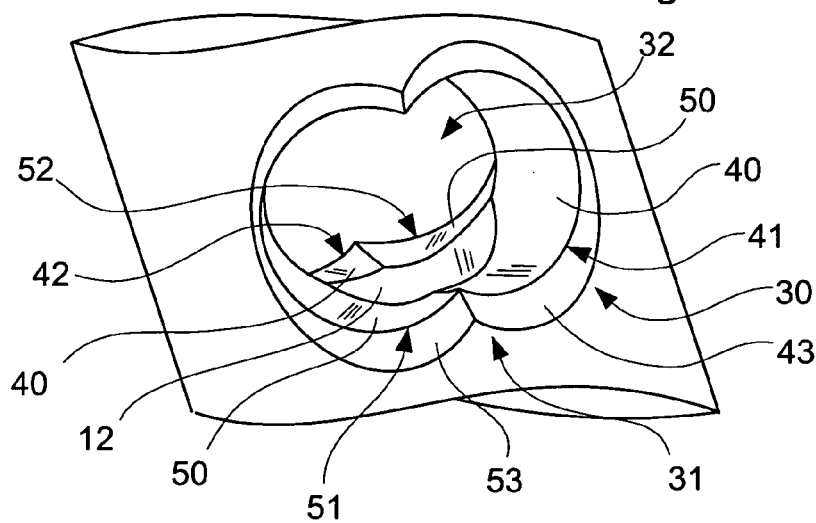
FIG. 3 is an isometric view of a polyaxial hole arrangement with two bores.

As can be additionally seen in FIG. 3, the first bore 40 starting in the front right extends to the intramedullary nail 1 to the back left, and correspondingly the second bore 50 extends from front left to back right. The first opening 31 of the polyaxial hole arrangement is the complete opening at the front in FIG. 3, formed by a first orifice 41 of the first bore 40 together with a first orifice 51 of the second bore 50. The second opening 32, in the back of the intramedullary nail in FIG. 3, is formed by a second orifice 52 of the second bore 50 together with a second orifice 42 of the first bore 40.

The intersecting bores, when viewed from either side of the nail, form an "8" shape with the "8" lying along a direction orthogonal to the nail axis. The narrowest dimension of the "8" on both sides of the nail is located midway between the intersecting bores if the bores have the same diameter and extends at least partially through the nail.

Figure 4:
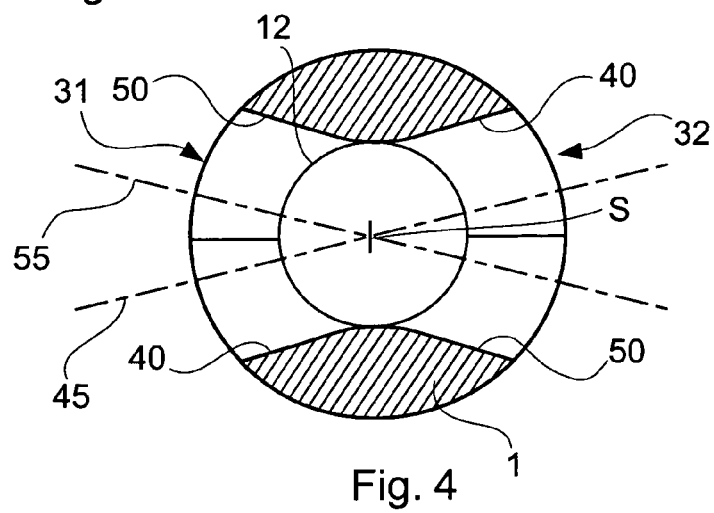
FIG. 4 is a section view showing the inner space formed by two intersecting bores.
Figure 2B:
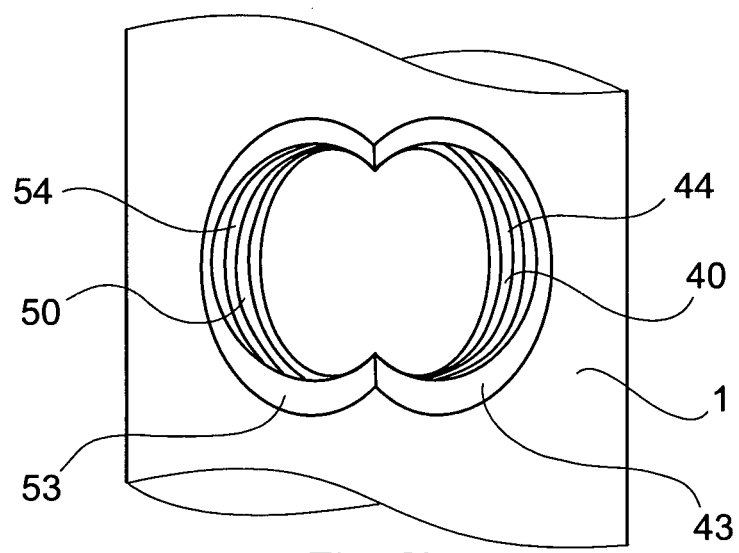
FIG. 2b is a detail view of a polyaxial hole arrangement with two bores including threads.

As can be seen in FIG. 4, the axis 45 of the first bore 40 is inclined with respect to the axis 55 of the second bore 50, and furthermore the axis 45 intersects with the axis 55 substantially at the centre of the intramedullary nail 1. Due to the two crossing bores, the first bore 40 comprises a wall substantially at the right side, when seen from the left in FIG. 4, and having a wall substantially at the left side, when extending through the intramedullary nail 1 to the right side in FIG. 4. Correspondingly, the second bore 50 comprises a wall substantially at the left side, when seen from the left side in FIG. 4, and a wall substantially at the right side, when extending through the intramedullary nail to the right in FIG. 4. The intersection point between the axis 45 and 55 is denoted with S.

When introducing a locking screw through the polyaxial hole arrangement, it is possible that a locking screw 2 extends following the first bore 40 or otherwise following the second bore 50. These two possibilities are both illustrated in FIG. 5.

Figure 5:
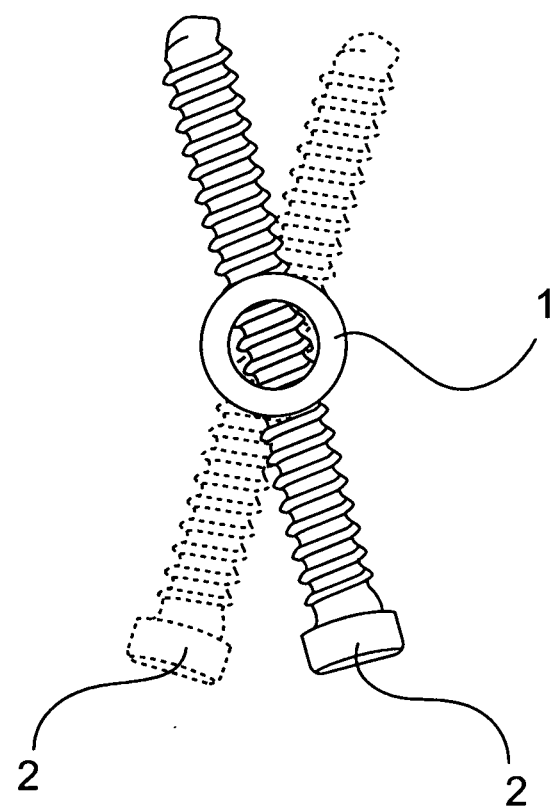
FIG. 5 illustrates orientations of a locking screw located in any one of the first and second bore.

Further shown in FIGS. 3, 4 and 5 is a bore 12 extending in a longitudinal direction of the intramedullary nail 1 and accordingly intersecting the polyaxial hole arrangement 30. It is noted that such a longitudinal bore 12 may extend completely through the intramedullary nail or at least partially through the nail. In case of a curved nail, such a bore or channel may extend along a centerline of the curved nail.

FIGS. 6 to 9 illustrate a further embodiment according to the invention, wherein the polyaxial hole arrangement comprises three intersecting bores.

Figure 6A:
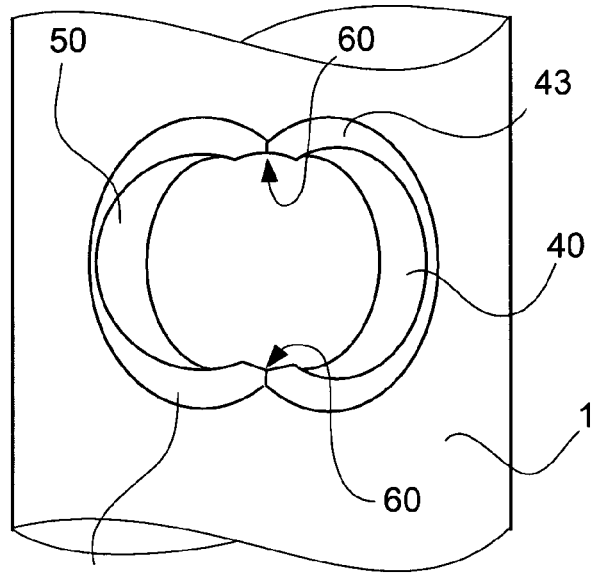
FIG. 6a illustrates a polyaxial hole arrangement with three bores.
Figure 6B:
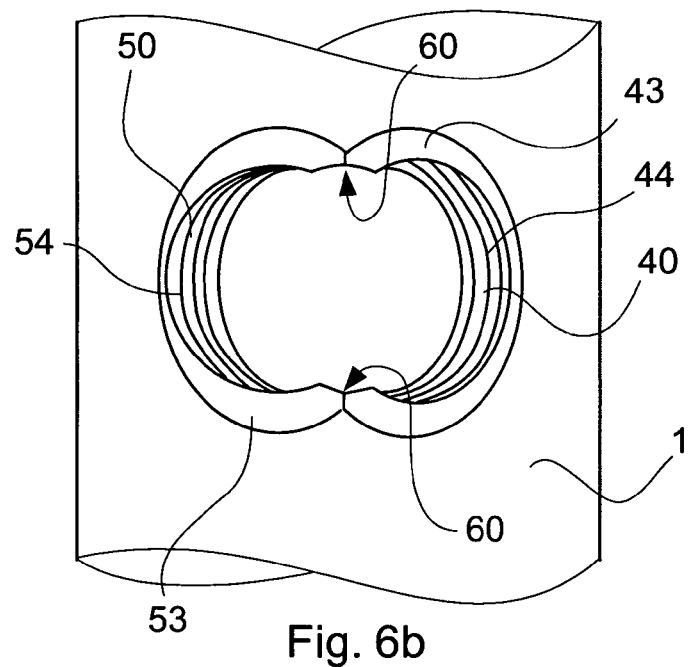
FIG. 6b illustrates a polyaxial hole arrangement with three bores including threads.

FIG. 6a illustrates the contour of the polyaxial hole arrangement including a first bore 40, a second bore 50, and the third bore 60, wherein the first bore 40 comprises a chamfer 43, and the second bore 50 comprises a chamfer 53. FIG. 6b differs from FIG. 6a in that at least the first bore 40 and the second bore 50 are provided with threads 44 and 54, respectively. It is noted that, although not visible, also the third bore 60 may be provided with threads.

The intersecting bores, when viewed from either side of the nail, form substantially an "8" shape with the "8" lying along a direction orthogonal to the nail axis. At the narrowest dimension of the "8", upper and lower arcuate sections 60 are present on both sides of the nail intermediate the first and second circular bores. The arcuate sections also extend at least partially through the nail.

Figure 7:
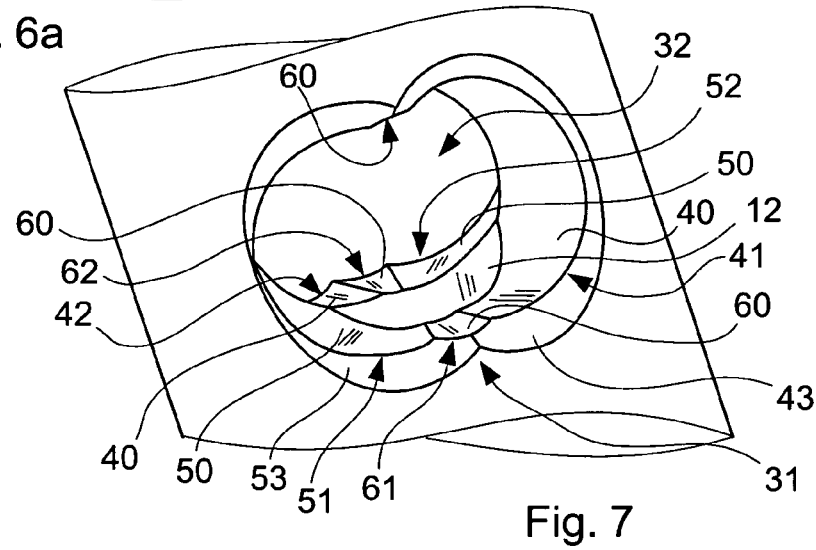
FIG. 7 is an isometric view showing the polyaxial hole arrangement with three bores.

As can be seen from in the isometric view of FIG. 7, the first bore 40 extends from the first orifice 41 and the chamfer 43 at the front of FIG. 7 to the back left side of the polyaxial hole arrangement in FIG. 7, with its second orifice 42. The second bore 50 extends from the chamfer 53 and the first orifice 51 at the front left of FIG. 7 to the back right of FIG. 7, with the second orifice 52. The third bore 60 forming a first orifice 61 at the front of FIG. 7, extends in the middle through the polyaxial hole arrangement to the second orifice 62. A first opening 31, at the front in FIG. 7, is formed by the first orifice 41 of the first bore 40, the first orifice 61 of the third bore 60, and the first orifice 51 of the second bore 50. A second opening 32 is formed by the second orifice 42 of the first bore 40, the second orifice 52 of the second bore 50, and the second orifice 62 of the third bore 60.

Figure 8:
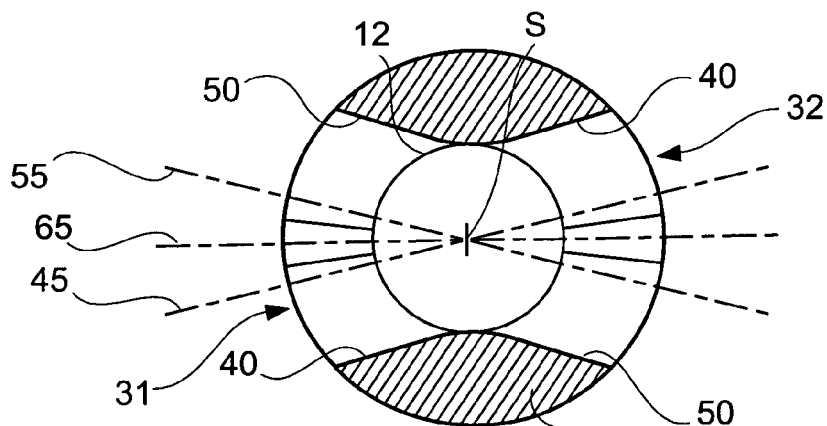
FIG. 8 is a section view showing the inner space formed by three bores with an intersection of the bore axes substantially at the center of the intramedullary nail.

Also in this embodiment, the polyaxial hole arrangement extends with a width in a transverse direction of the intramedullary nail 1 which is cut under and above the polyaxial hole arrangement. FIG. 8 shows, as a section view along a transverse plane through the intramedullary nail 1, a configuration in which the axis 45 of the first bore 40, the axis 55 of the second bore 50, and the axis 65 of the third bore 60 intersects at one point S substantially in the centre of the intramedullary nail 1.

Figure 9:
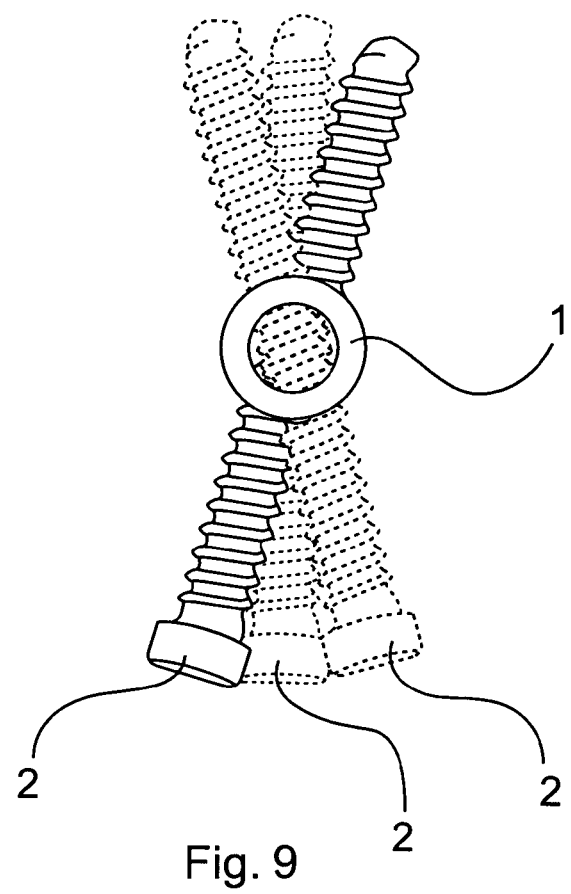
FIG. 9 illustrates orientations of a locking screw positioned in a respective bore of the polyaxial hole arrangement.

Consequently, a locking screw 2 may be introduced through the polyaxial hole arrangement in three ways. As shown in FIG. 9, a locking screw may be introduced along a centre axis as well as along a respective axis inclined to the left or to the right with respect to the centre axis. The centre axis may be orientated in a medio-lateral direction.

Figure 10:
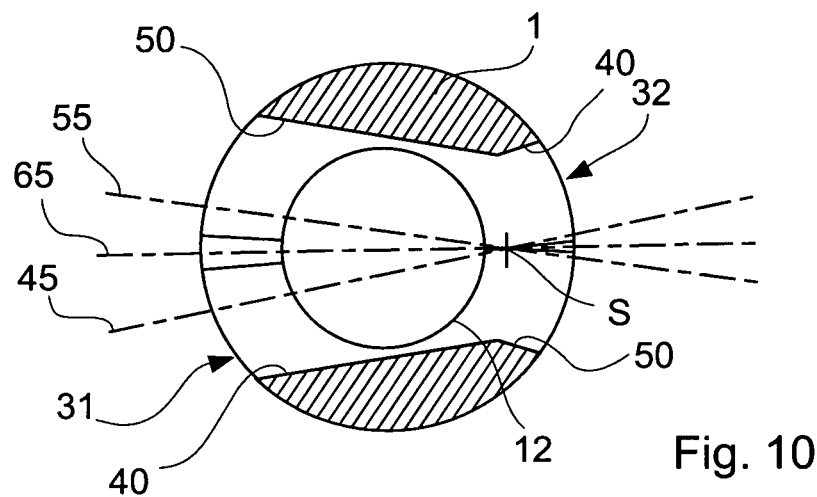
FIG. 10 is a section view showing an inner space formed by three bores with an intersection of the bore axes within the intramedullary nail.

In FIG. 10, another embodiment according to the invention is shown. The difference between this embodiment and the embodiment shown in FIG. 8 is that the intersection point S is displaced within the intramedullary nail in a direction to one side. In other words, the intersection point S is asymmetrically arranged with a smaller distance to the second opening 32 of the polyaxial hole arrangement and a larger distance to the first opening 31 of the polyaxial hole arrangement. Consequently, the wall sections of the side walls of the first bore 40 as well as of the second bore 50 are asymmetric.

Figure 11:
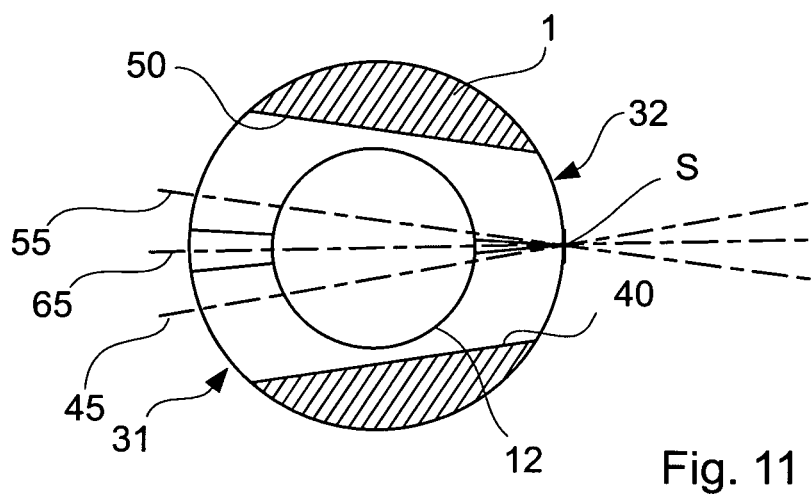
FIG. 11 is a section view illustrating the inner space formed by three bores with an intersection of the bore axes formed at an edge of the intramedullary nail.

In FIG. 11, a further embodiment of the invention is shown. Here, the intersection point S of the three axes 45, 55, 65 of the three bores is located at the edge of the cross section of the intramedullary nail 1. In other words, the intersection point S is located in the centre of the second opening 32 of the polyaxial hole arrangement. Accordingly, the first opening 31 includes a larger cross section as the second opening 32. From the intersection point S at the second opening 32, the three bores diverge in the direction to the first opening 31, which is indicated by the respective centre axis 45, 55, 65 of the three bores.

Figure 12:
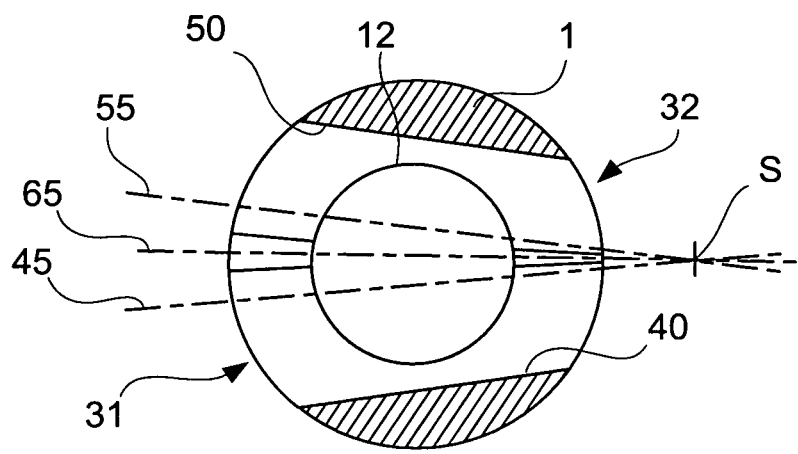
FIG. 12 is a section view of a polyaxial hole arrangement with three bores with an intersection of the bore axes outside the intramedullary nail.

In FIG. 12, yet another embodiment according to the invention is shown. In this embodiment, the intersection point S of the three axes 45, 55, 65 of the three bores is located outside the cross section of the intramedullary nail 1. Further shown in FIG. 12 is another inclination angle between the three axes, showing that the three bore axes may be inclined with respect to each other in different ways.

Further shown in FIGS. 7 to 12 is a bore 12 extending in a longitudinal direction of the intramedullary nail 1. Accordingly, the intramedullary nail 1 is a cannulated nail. It is noted that such a longitudinal bore may extend completely through the intramedullary nail or at least partially through the nail. In case of a curved nail, such a bore or channel may extend along a centerline of the curved nail.

Figure 13:
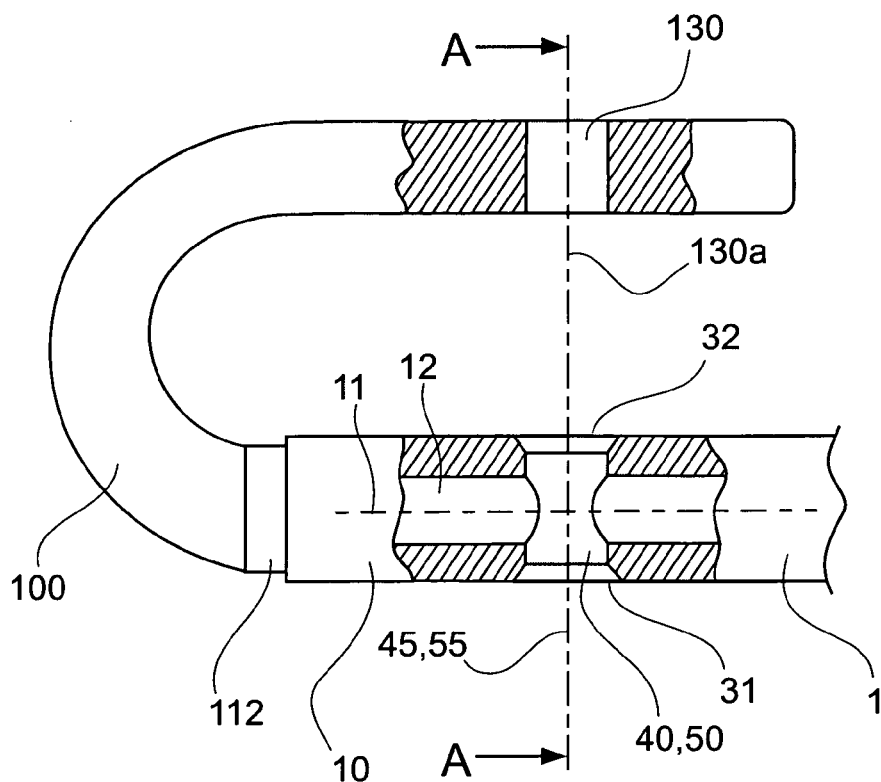
FIG. 13 shows a combination of a targeting device with an intramedullary nail.

FIG. 13 shows a combination of a targeting device 100 and an intramedullary nail 1. The targeting device 100 comprises a coupling portion 112 which is adapted to be coupled with the driving end portion 10 of the intramedullary nail 1. The targeting device 100 further comprises a drilling gauge 130 with a drilling axis 130a. The targeting device 100 is designed so that the drilling axis 130a of the drilling gauge 130 is aligned with the hole arrangement in the driving end portion 10 of the intramedullary nail 1. In this side view, the differing centre axis 45, 55 of the first bore 40 and the second bore 50, respectively, are arranged behind each other so that only one axis is illustrated.

Figure 14:
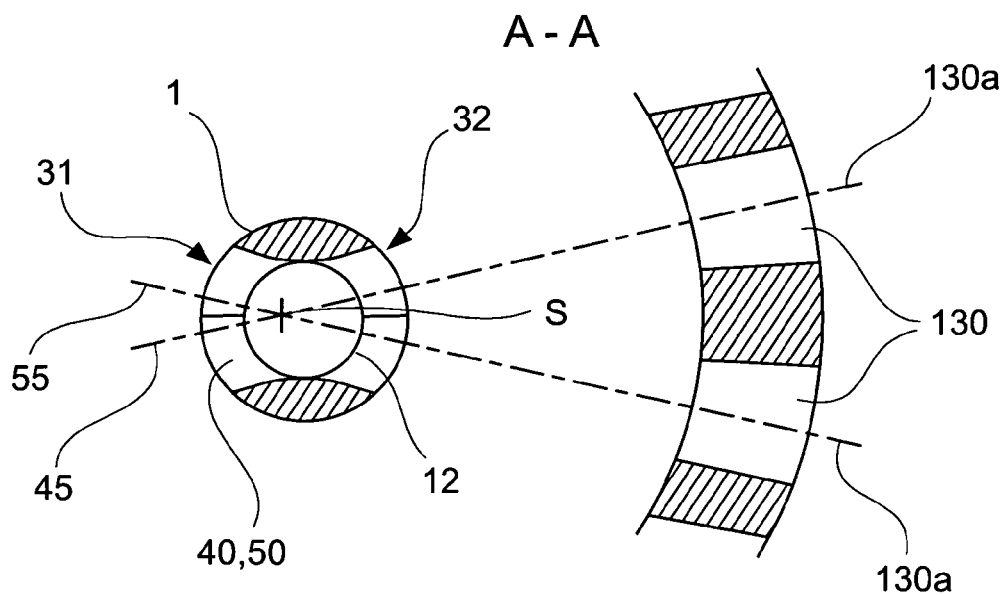
FIG. 14 is a section top view showing a targeting device with two drilling gauges in relation to a polyaxial hole arrangement with two bores.

FIG. 14 is a section view along the plane A-A of FIG. 13, including the centre axes 45, 55 of the first bore 40 and the second bore 50, respectively. As illustrated in FIG. 14, the targeting device 100 may include a drilling gauge 130 for each of the bores provided in the intramedullary nail. Accordingly, one drilling axis 130a is shown for each of the axes of the first and second bores. In this embodiment, the intersection of the bore axis is located within the cross section of the intramedullary nail.

It is noted that a targeting device usable with an intramedullary nail having a polyaxial hole arrangement with three intersecting bores, may comprise three corresponding drilling gauges with respective drilling axes.

Although the intramedullary nail is illustrated in the figures as a cannulated nail, i.e. the nail comprises a bore or channel in a longitudinal direction of the nail, it will be understood that the intramedullary nail may also be solid, i.e. without such a channel.

Figure 15:
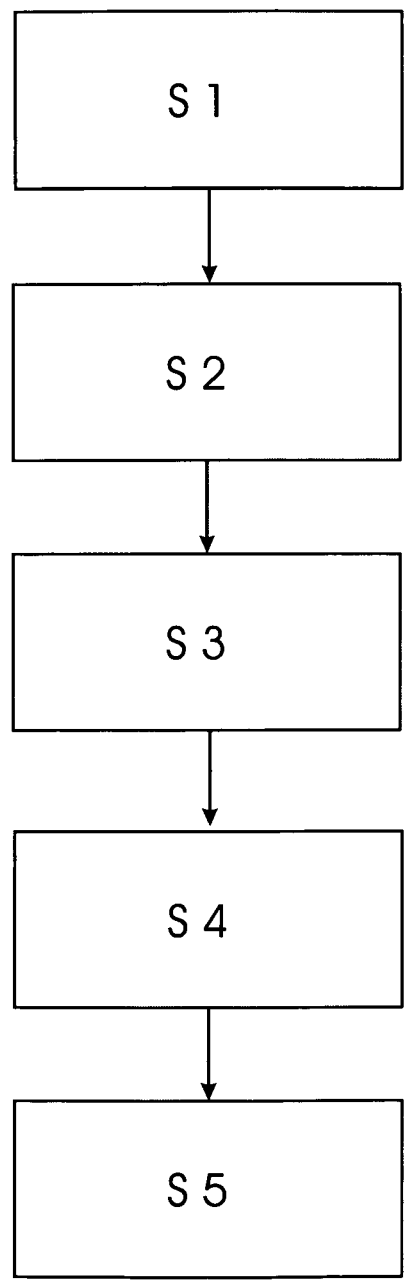
FIG. 15 is a flowchart illustrating steps of a method according to the invention.

The flowchart in FIG. 15 illustrates the steps of a method in accordance with the invention. It will be understood that the steps described, are major steps, wherein these major steps might be differentiated or divided into several sub-steps. Furthermore, there might be also sub-steps between these major steps. Therefore, a sub-step is only mentioned if this step may be important for the understanding of the principles of the method according to the invention.

In step S1, the intramedullary nail is introduced into a medullary channel of a fractured bone.

In step S2, a fracture line of the bone relative to the intramedullary nail is identified.

In step S3, a targeting device may be coupled to the proximal end of the intramedullary nail, the targeting device including a drilling gauge corresponding to the bores of the polyaxial hole arrangement.

In step S4, one bore from the bores of the polyaxial hole arrangement is selected, which bore is suitable depending on the identified fracture line.

In step S5, a locking screw is screwed through the selected bore and through and into the bone. In case, a targeting device is utilized, the drilling tool will be guided by the drilling gauge.

By way of the method according to the invention, firstly fractured parts of a bone can be reliably secured to each other and secondly an intramedullary nail can be reliably fixed within the fractured bone.

While the invention has been illustrated and described in detail in the drawings and foregoing description, such illustration and description are to be considered illustrative or exemplary and not restrictive. The invention is not limited to the disclosed embodiments.

Other variations to the disclosed embodiments can be understood and effected by those skilled in the art in practising the claimed invention, from the study of the drawings, the disclosure and the dependent claims. In the claims, the word "comprising" does not exclude other elements and identified article "a" or "an" does not exclude a plurality. The mere fact that certain measures are recited in mutual different dependent claims does not indicate that a combination of these measures cannot be used to advantageous. Any reference signs in the claims should not be construed as limiting the scope.

LIST OF REFERENCE SIGNS 1 intramedullary nail
2 locking screw
10 driving end portion
11 longitudinal axis of driving end portion
12 longitudinal bore
20 non-driving end portion
21 longitudinal axis of non-driving end portion
30 locking hole arrangement
31 first opening
32 second opening
40 first bore
41 first orifice of first bore
42 second orifice of first bore
43 chamfer
44 thread
45 axis of first bore
50 second bore
51 first orifice of second bore
52 second orifice of second bore
53 chamfer
54 thread
55 axis of second bore
60 third bore
61 first orifice of third bore
62 second orifice of third bore
65 axis of third bore
100 targeting device
112 coupling portion
130 drilling gauge
130a drilling axis
S intersection point

The invention claimed is:

1. An intramedullary nail, comprising:
a locking hole arrangement having a first opening on one side of the intramedullary nail and a second opening at an opposing side of the intramedullary nail;
wherein the locking hole arrangement comprises a first bore having a first bore axis, and a second bore having a second bore axis and a third bore having a third bore axis;
wherein the first bore, the second bore and the third bore each forming a first orifice on one side of the intramedullary nail and each forming a second orifice at an opposing side of the intramedullary nail, each of the first, second and third bores forming the first and second orifices having proximal and distal arcuate facing boundaries, wherein the first bore axis and the second bore axis are inclined with respect to each other, wherein the first bore and the second bore intersect each other;

wherein the first orifice of the first bore, the first orifice of the second bore and the first orifice of the third bore together form the first opening of the locking hole arrangement;

wherein the second orifice of the first bore, the second orifice of the second bore and the second orifice and the third bore together form the second opening of the locking hole arrangement; and the third bore extending between the first and second bores in an area where the first and second bores intersect the third bore to form the proximal and distal arcuate facing boundaries of the first and second orifices, the proximal and distal arcuate facing boundaries each comprising three connected concave arcuate sections formed by the first, second, and third bores respectively, wherein the arcuate sections of the third bore being smaller than the arcuate sections of the first and second bores.

2. The intramedullary nail according to claim 1, wherein locking hole arrangement is arranged in a driving end portion of the intramedullary nail.

3. The intramedullary nail according to claim 1, wherein the first bore axis and the second bore axis intersect each other.

4. The intramedullary nail according to claim 1, wherein a minimum distance of the first bore axis and the second bore axis lies within the intramedullary nail.

5. The intramedullary nail according to claim 1, wherein a minimum distance of the first bore axis and the second bore axis lies on a longitudinal centre axis of the intramedullary nail.

6. The intramedullary nail according to claim 1, wherein the first bore axis and the second bore axis are inclined with respect to each other and orthogonal to a longitudinal centre axis of the intramedullary nail.

7. An intramedullary nail, comprising:
a locking hole arrangement having a first opening on one side of the intramedullary nail and a second opening at an opposing side of the intramedullary nail,
wherein the locking hole arrangement comprises a first bore having a first bore axis, a second bore having a second bore axis, and a third bore having a third bore axis,
wherein the first bore, the second bore and the third bore forms the first opening on one side of the intramedullary nail and forms the second opening at an opposing side of the intramedullary nail, the first, second and third bores defining proximal and distal facing boundaries of each first and second opening;
wherein the first bore axis, the second bore axis and the third bore axis are inclined with respect to each other;
wherein the third bore is intermediate the first bore and the second bore; and
the proximal and distal facing boundaries of the first and second openings each have three connected concave arcuate sections formed by the first, second and third bores respectively, with the concave arcuate sections of the third bore intersecting the concave arcuate sections of the first and second bores, wherein the arcuate sections of the third bore being smaller than the arcuate sections of the first and second bores.

8. The intramedullary nail according to claim 7, wherein the first bore axis, the second bore axis and the third bore axis intersect within the intramedullary nail.

9. The intramedullary nail according to claim 7, wherein the first bore axis, the second bore axis and the third bore axis intersect a longitudinal centre axis of the intramedullary locking nail.

10. The intramedullary nail according to claim 7, wherein the first bore axis, the second bore axis and the third bore axis are each inclined with respect to each other and orthogonal to a longitudinal centre axis of the intramedullary nail.

11. The intramedullary nail according to claim 7, wherein the third bore axis has an orientation corresponding to the medio-lateral direction.

12. The intramedullary nail according to claim 7, wherein the first bore axis is inclined by plus 15° over the third bore axis and the second bore axis is inclined by minus 15° over the third bore axis.

13. The intramedullary nail according to claim 1, wherein the at least one of the first opening and second opening comprise a chamfer with respect to the respective orifice of the first bore and the respective orifice of the second bore.

14. The intramedullary nail according to claim 1, wherein at least one of the first bore, the second bore and the third bore comprises a thread.

15. An intramedullary nail, comprising:
a body having a first body portion extending along a longitudinal axis;
a locking hole arrangement in the first body portion having a first opening on one side of the intramedullary nail and a second opening at an opposing side of the intramedullary nail;
wherein the locking hole arrangement comprises a first bore having a first bore axis, a second bore having a second bore axis, and a third bore having a third bore axis, the first, second and third bore axis lying in a plane extending transverse to the longitudinal axis, the third bore axis intermediate the first and second axis of the first and second bores, the first, second and third bore axis intersecting;
wherein the first bore, the second bore and the third bore each forming a first orifice on one side of the intramedullary nail and each forming a second orifice at an opposing side of the intramedullary nail, the first and second orifices having proximal and distal facing sides each comprising three concave arcuate sections, the concave arcuate sections formed by the first, second and third bores, wherein the arcuate sections of the third bore being smaller than the arcuate sections of the first and second bores;
wherein the first bore axis, the second bore axis and the third bore axis are angled with respect to each other in the plane and intersect within the nail body first portion;
wherein the first orifice of the first bore, the first orifice of the second bore, and the first orifice of the third bore together form the first opening of the locking hole arrangement;
wherein the second orifice of the first bore, the second orifice of the second bore and the second orifice of the third bore together form the second opening of the locking hole arrangement; and
the concave arcuate portion of the third bore intermediate the concave arcuate portions of the first and second bores, the concave arcuate section of the third bore intersecting the concave arcuate sections of the first and second bores.

16. The intramedullary nail according to claim 15, wherein the first bore axis, the second bore axis and the third bore axis intersect a longitudinal centre axis of the intramedullary locking nail.

17. The intramedullary nail according to claim 15, wherein the plane containing the first bore axis, the second bore axis and the third bore axis is each and orthogonal to the longitudinal axis of the intramedullary nail first body position.

18. The intramedullary nail according to claim 15, wherein the third bore axis has an orientation corresponding to the medio-lateral direction.

* * * * *